United States Patent [19]

Holen et al.

[11] Patent Number: 4,883,763
[45] Date of Patent: Nov. 28, 1989

[54] SAMPLE PROCESSOR CARD FOR CENTRIFUGE

[75] Inventors: James T. Holen, Mundelein; Vidas P. Kazlauskas, Waukegan, both of Ill.

[73] Assignee: Abbott Laboratories, Chicago, Ill.

[21] Appl. No.: 253,370

[22] Filed: Sep. 30, 1988

Related U.S. Application Data

[63] Continuation of Ser. No. 882,734, Jul. 7, 1986, abandoned, which is a continuation-in-part of Ser. No. 861,477, May 9, 1986, abandoned, which is a continuation of Ser. No. 606,785, May 3, 1984, abandoned.

[51] Int. Cl.$^4$ .................. G01N 21/84; B01L 3/00
[52] U.S. Cl. ..................... 436/45; 356/246; 356/426; 356/427; 422/72; 422/102; 436/165; 436/177
[58] Field of Search ........... 422/58, 61, 72, 102, 422/104; 436/45, 165, 177, 180; 356/426, 422, 246; 250/576

[56] References Cited

U.S. PATENT DOCUMENTS

| | | | |
|---|---|---|---|
| 3,211,368 | 10/1965 | Stanley | 494/10 |
| 3,532,470 | 10/1970 | Rochte | 422/61 |
| 3,795,451 | 3/1974 | Mailen | 250/576 |
| 3,829,223 | 8/1974 | Hamil | 422/72 |
| 4,256,096 | 3/1981 | Soodak . | |
| 4,390,499 | 6/1983 | Curtis | 422/102 |
| 4,431,606 | 2/1984 | Revillet et al. . | |
| 4,469,793 | 9/1984 | Guigan | 422/72 |
| 4,515,889 | 5/1985 | Klose et al. | 422/64 |
| 4,557,600 | 12/1985 | Klose et al. . | |

FOREIGN PATENT DOCUMENTS

2524874 10/1983 France .

*Primary Examiner*—Michael S. Marcus
*Attorney, Agent, or Firm*—Thomas D. Brainard; Donald L. Corneglio; Edward H. Gorman, Jr.

[57] ABSTRACT

A sample processor card for use with a centrifuge in which the direction of centrifugal force can be altered at will, wherein the card includes a supply of chemical reagent and inlet means for supplying a chemical sample to the card. The sample is advanced under centrifugal force through capillary means to sample measuring means, and the measured sample is then mixed with reagent to permit a chemical test to be carried out on the reagent, all under centrifugal force.

21 Claims, 4 Drawing Sheets

SAMPLE PROCESSOR CARD FOR CENTRIFUGE

CROSS-REFERENCE TO RELATED PATENT APPLICATIONS

This application is a continuation of application Ser. No. 882,734, filed July 7, 1986, now abandoned; which is a continuation-in-part of Ser. No. 861,477, filed May 9, 1986, now abandoned; which is a continuation of Ser. No. 606,785, filed May 3, 1984, now abandoned.

BACKGROUND OF THE INVENTION

This invention relates to a method and apparatus for chemical testing, and more particularly to apparatus for carrying out chemical testing and a method for using same.

In copending application Ser. No. 856,078 filed Apr. 25, 1986, the disclosure of which is incorporated herein by reference, there is described apparatus for carrying out chemical testing in which samples and/or reagents are manipulated by means of centrifugal force. The reagents and samples are placed in a sample processor device which is then placed in a centrifuge and subjected to high centrifugal forces. Manipulation of the reagents and samples in the sample processing device is achieved by rotating the device relative to the centrifuge itself so that the direction of centrifugal force acting on the device is changed.

SUMMARY OF THE INVENTION

The present invention relates to the sample processor device and method by which it is used.

It is an object of the present invention to provide a sample processing card for use in a centrifuge of the type described for carrying out chemical testing.

It is a more specific object of the invention to provide a sample processing device in which chemical testing of a sample can be carried out under the effect of centrifugal force.

It is a further object of the invention to provide a sample processing device and method for its use wherein the device can be provided with a stored reagent therein, ready for use in response to application of centrifugal force to the device, in which a chemical test can be carried out supplying a sample thereto and then applying centrifugal forces acting in two or more directions thereto to effect transfer of liquids from one chamber therein to another.

These and other objects and advantages of the invention will appear more fully hereinafter, and, for purposes of illustration, but not of limitation, embodiments of the invention are shown in the accompanying drawings.

DETAILED DESCRIPTION OF THE INVENTION

Figure 1:
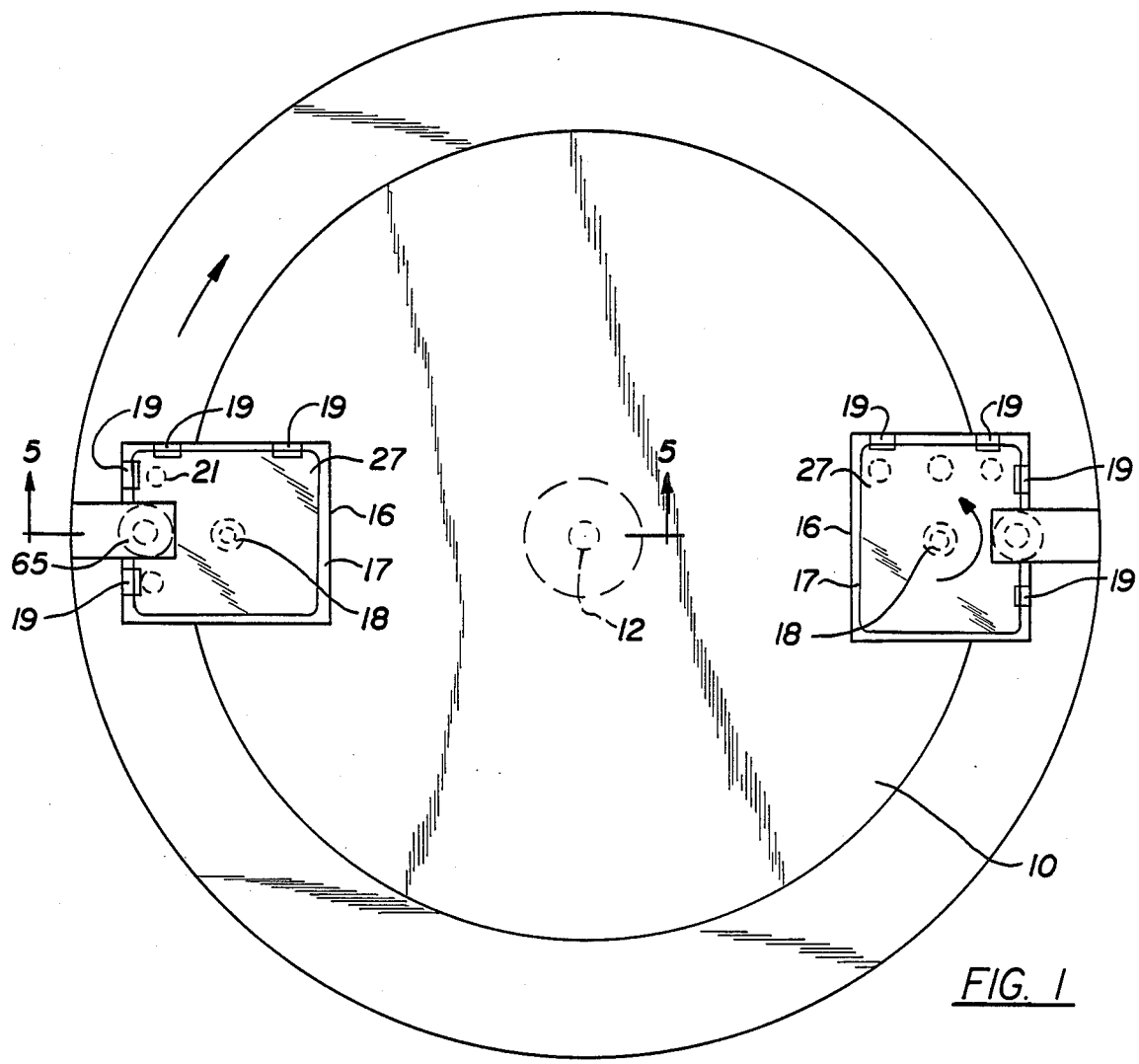
FIG. 1 is a top view of a schematic diagram of centrifuge apparatus employed in the practice of the invention.

The concepts of the present invention reside in a sample processor card and method for its use wherein the sample processor card is formed of a substantially closed chamber which includes a supply of reagent therein. The card includes inlet means for supplying a sample to the card; capillary means communicating with the inlet means to receive a sample supplied to the card and overflow means communicating with the capillary means to receive excess sample which is advanced from the inlet means through the capillary means under the influence of centrifugal force applied to the card in a first direction. The card also includes holding chamber means adapted to receive reagent from the reagent supply and sample from the capillary means in response to centrifugal force acting on the card in a second direction, and cuvette means communicating with the holding chamber means which is adapted to permit the measurement of the chemical reaction between the reagent and the sample. Thus, by use of the sample processor card of the invention, flow of the reagent and the sample within the card is achieved solely by centrifugal force acting in two or more directions on the card as the card is subjected to high centrifugal forces in a centrifuge.

The sample processor card of the present invention can be used in any of a wide variety of analytical chemical techniques, including testing to determine blood chemistries, immunological testing for analyzing fluids and particularly body fluids as well as a number of other liquid analytical chemical techniques. The card of the present invention is particularly adapted to perform blood chemistries in which the sample supplied to the card is a whole blood sample.

In accordance with that preferred embodiment of the invention, the card of the present invention also includes a sample separating chamber which communicates with the capillary means to separate the solid constituents of blood from the liquid constituents. Thus, the sample separating chamber is positioned to receive sample from the capillary means which is caused to flow into the sample separating chamber under the influence of centrifugal force and therein caused to be separated by the centrifugal force. By providing the card with a sample separating chamber, it is possible to supply to the card a sample of whole blood which has not been previously spun down to separate liquid constituents from the solid constituents. That enables an operator to avoid a separate manipulative step of separating the whole blood before subjecting the sample of whole blood to chemical analysis.

Because most blood chemistry tests require the use of precisely measured samples, in the preferred practice of the invention, the sample processor card also includes a sample measuring chamber communicating with the capillary means or the sample separating chamber which is adapted to receive a measured quantity of sample in response to centrifugal force applied to the card. The sample measuring chamber is positioned adjacent to a sample overflow chamber which receives sample in excess of that filling the sample measuring chamber, the excess sample being retained in the sample overflow chamber as the direction of the centrifugal force is changed to cause the measured sample to be displaced from the sample measuring chamber to the sample holding chamber where it is mixed with the reagent in carrying out the chemical test under the effect of centrifugal force.

In another preferred embodiment of the invention, the sample processor card is provided with a supply of reagent in the form of means for dispensing reagent in response to centrifugal force applied to the card. By providing the card with a built-in supply of reagent, the card can be used by supplying a sample thereto and then subjecting the card to the effect of centrifugal force to release the reagent for admixing with the sample to carry out the chemical testing operation. Further, means for accurately measuring and mixing the reagent can be provided by passages and chambers in order to carry out complicated test methods.

In one preferred embodiment, the means for dispensing the reagent(s) comprises a reagent chamber which is adapted to contain the reagent(s) and a strippable sealing means for closing the reagent chamber. When the sealing means is stripped from the reagent chamber in response to the application of centrifugal force to the card the reagent(s) are released. In another preferred embodiment, the means for dispensing the reagent(s) comprises reagent chamber(s) which is adapted to contain the reagent(s) and a means for puncturing the chamber(s) in response to the application of centrifugal force to the card whereby the reagent(s) are released.

It is sometimes desirable that the reagent, by reason of its stability characteristics, be packaged separately from a reagent diluent. In one preferred embodiment of the invention, the application of centrifugal force to the card can serve to release both reagent and diluent either simultaneously or sequentially. Other reagents can be employed in solid form, for example, by placing a pellet in a compartment of the card where it will be subsequently dissolved by a liquid reagent released from the reagent chamber(s).

Figure 2:
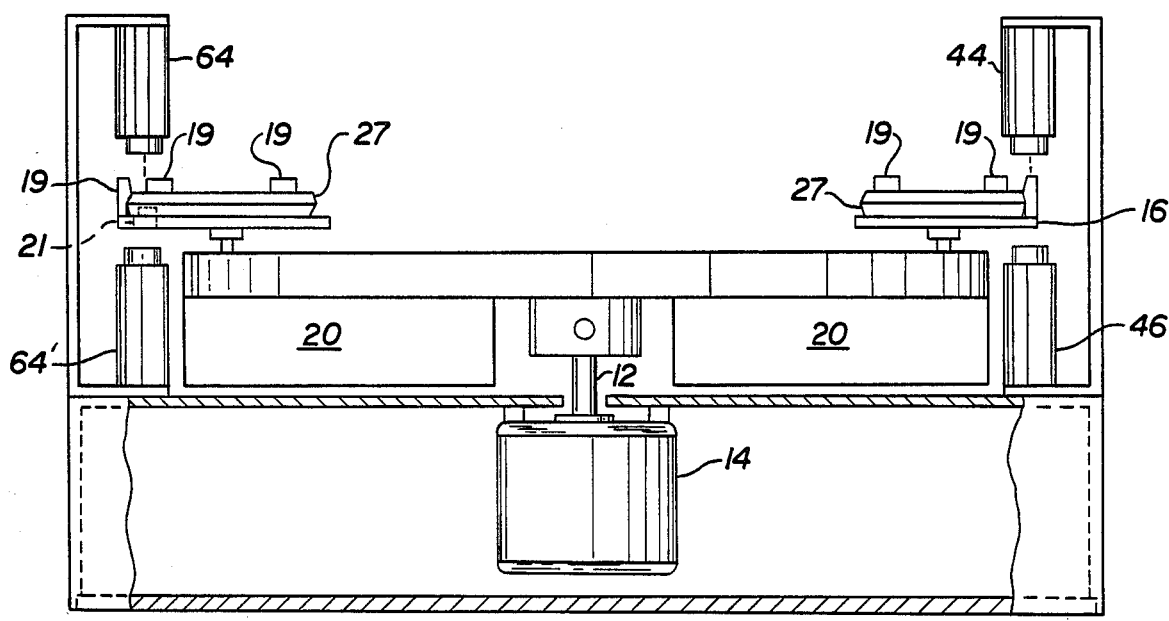
FIG. 2 is a side elevational view partially broken away of the apparatus shown in FIG. 1.

Referring now to the drawings for a more detailed description of the invention, there is shown in FIGS. 1-9 a schematic illustration of apparatus embodying the concepts of the present invention. As shown in FIG. 1, the centrifuge includes a plate member 10 which is mounted on an axis 12 for rotation about the axis. The plate member 10 is preferably driven by suitable drive means 14 which may be, for example, an electric motor capable of operating at high speeds as shown in FIG. 2. While plate member 10 is shown in FIG. 1 as a circular plate, it will be understood that its configuration as shown is not critical to the practice of the invention. For example, it is equally possible to use a centrifugal arm mounted for rotation about an axis.

Mounted on plate member 10 is at least one sample processor card holder 16 adapted to receive a sample processor card described more fully hereinafter. As is shown in FIGS. 1 and 2, the card holder 16 is in the nature of a tray and is rotatably mounted relative to the plate member 10 on an axis 18 operatively connected to means 20 to rotate the holder 16.

While the axis of rotation of the plate member 10 is illustrated in FIG. 2 as mounted on a vertical axis, it will be understood by those skilled in the art that the direction of the axis is not critical to the practice of the invention, and the axis, while preferably vertical, can also be horizontal or inclined in any direction since the effect of gravity on the sample processor card rotating with the plate member 10 is negligible.

In the preferred practice of the invention, the holder 16 can be rotated or indexed relative to the plate member 10 by any suitable drive means 20. In the preferred embodiment of the present invention, the holder 16 can be rotated or indexed 90° by the drive means 20. As will be appreciated by those skilled in the art, the holder 16 can be rotatable by an amount greater than 90° up to and including rotatable about a full 360°. The important feature is that the holder 16 adapted to receive the sample processor card be rotatable relative to the plate member 10 so that the direction of the centrifugal force acting on the sample processor card can be altered to effect the necessary fluid transport functions during the chemical testing operation.

Figure 3:
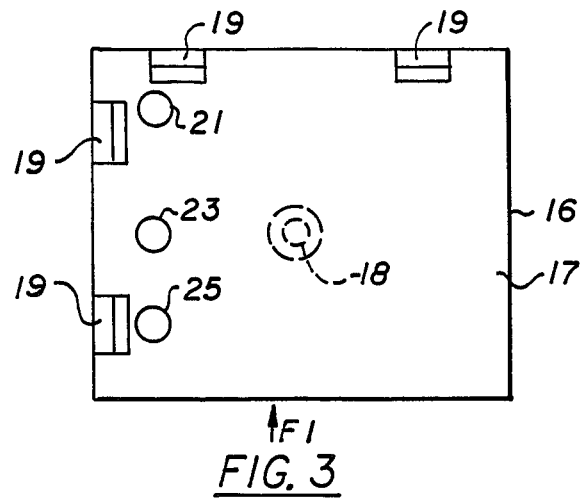
FIG. 3 is a plane view of a sample processor card holder.

With respect to the present invention, a sample processor card holder is illustrated in FIG. 3 of the drawing and includes a substantially flat plate portion 17 rotatable about the axis 18. The holder is provided with a plurality of finger-like projections 19 positioned at the periphery of the plate portion 17. As will be appreciated by those skilled in the art, use can be made of projections 19 about the entire periphery of the plate member 17. However, it is generally preferred to employ the projections only along those edges in the direction in which the centrifugal force is exerted on the holder 16 and hence a sample processor card mounted on it. Accordingly, FIG. 3 has been shown as illustrating finger-like projections 19 along only two edges of the plate member 17 since those edges are the direction in which the centrifugal force operates in the preferred embodiment of the invention.

As shown in FIG. 3 of the drawing, the holder 16 includes a pin 21 mounted on the plate member 17 so as to position the sample processor card on the holder, as will be described more fully hereinafter. In addition, the plate member 17 includes portions 23 and 25 in the surface thereof which are permeable to light; these portions are preferably openings in the plate 17 to permit the passage of light therethrough, as will also be described more fully hereinafter.

Referring to FIGS. 4 to 7 for a description of the sample processor card of the invention, there is shown two embodiments of sample processor cards (FIGS. 4 and 5) formed of a molded plastic article having outer walls 22 and 22' which, along with face plate 24 and bottom plate 26 define a unitary chamber. Within the chamber are a plurality of partitions defining the flow paths of the liquids during the chemical testing operation.

Sample can be introduced to the sample processor card by any of a variety of techniques. In accordance with one embodiment of the invention, the face plate 24 includes an opening 28 therein into which a blood sample, for example, may be deposited for analysis. Alternatively, there can be provided an opening 53 into which a capillary is placed to introduce a blood sample into a capillary slot 34 defined by two interior walls 30 and 32. In either case, blood introduced through the opening 28 or the opening 53 is moved through the capillary slot 34 by means of centrifugal force acting in a first direction $F_O$.

As will be appreciated by those skilled in the art, the techniques involving the use of sample processor card 27 are applicable to any liquid to be subjected to chemical testing. In addition to whole blood, use can also be made of pre-spun blood fractions or other body fluids to be analyzed. Of course, the concepts of the present invention are equally applicable to other liquids which do not originate in the body on which chemical testing is conducted. For ease of description, however, the following describes the use of the sample card 27 using whole blood as the starting sample.

In one embodiment of the invention, the sample processor card also includes a reagent chamber 86 and a diluent chamber 88 which operate, in response to centrifugal force acting in the direction $F_0$ to release reagent and diluent. The essential feature of such a container is that it releases the diluent and reagent in response to centrifugal force acting upon the card 27.

One means for releasing the reagent and/or diluent is shown in FIGS. 4, 6, 7, and 8. The reagent chamber 86 is a substantially closed container open at its lower portion 31. Closing that lower portion 31 is a removable strip 33 formed of an adhesive portion 35 which adheres to the side walls 37 of chamber 86 and a structural portion 39 underlaying the adhesive portion 39 and fixed to the card 27 such as by means of a pin or pins placed through the pin holes 41'.

Figure 6:
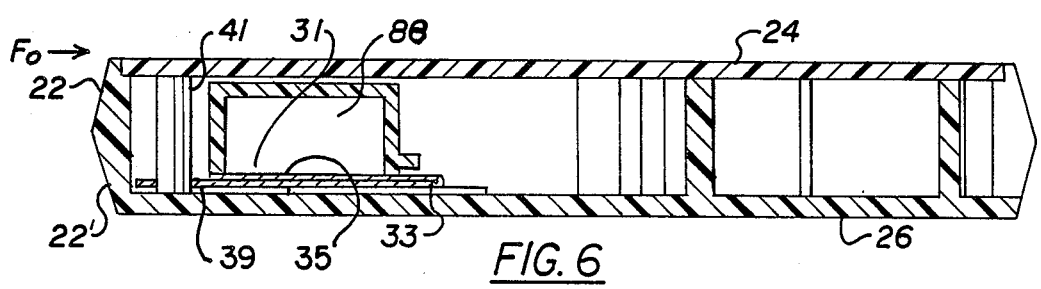
FIG. 6 is a sectional view taken along the line 6—6 in FIG. 4.
Figure 7:
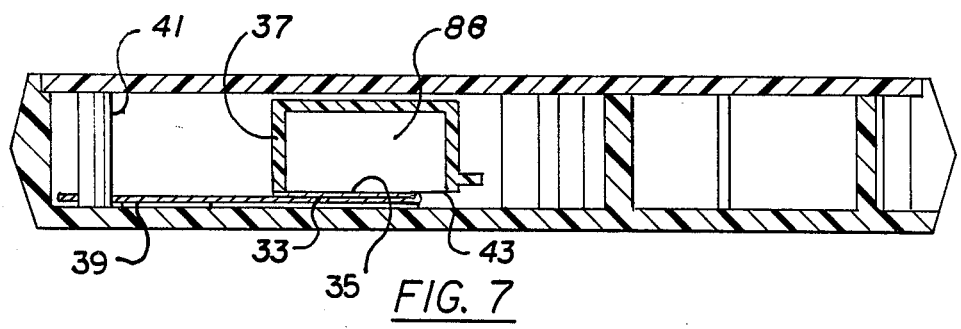
FIG. 7 is a sectional view like that of FIG. 6, after the application of centrifugal force thereto.
Figure 8:
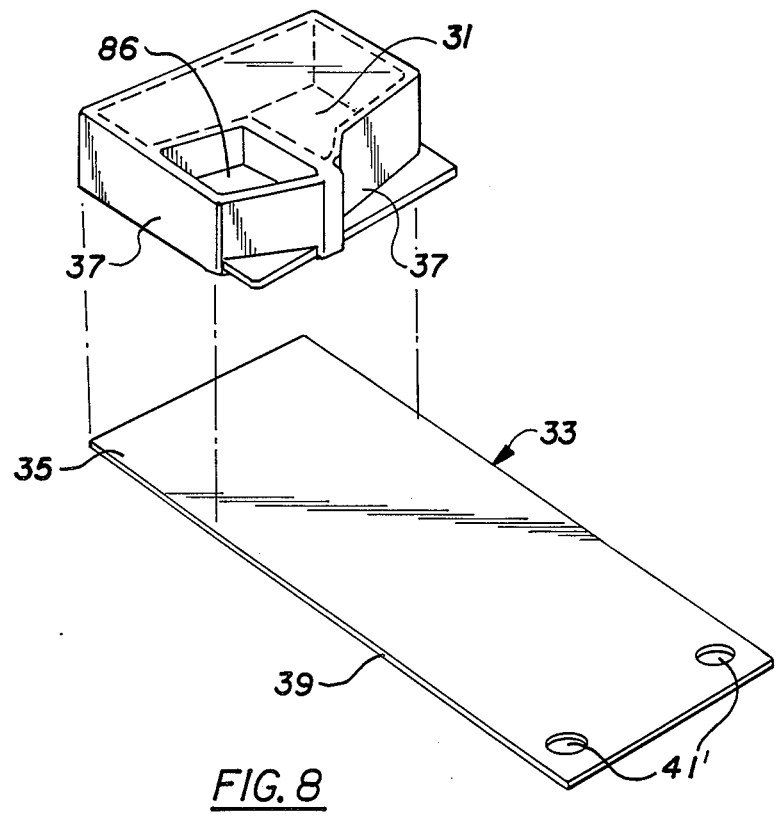
FIG. 8 is an exploded view of one embodiment for a reagent container of the invention.

As the card is subjected to centrifugal force in the direction $F_O$, the chambers 86 and 88 are is displaced to the right as shown in FIGS. 6 and 7. Meanwhile, the removable strip 33 is held in position because of its attachment to the card 27 by the pins 41, thereby peeling the removable strip 33 from the chamber 86 and 88 and releasing reagent through the opening, 43 thus formed between the strip 33 and side walls 37.

Figure 5:
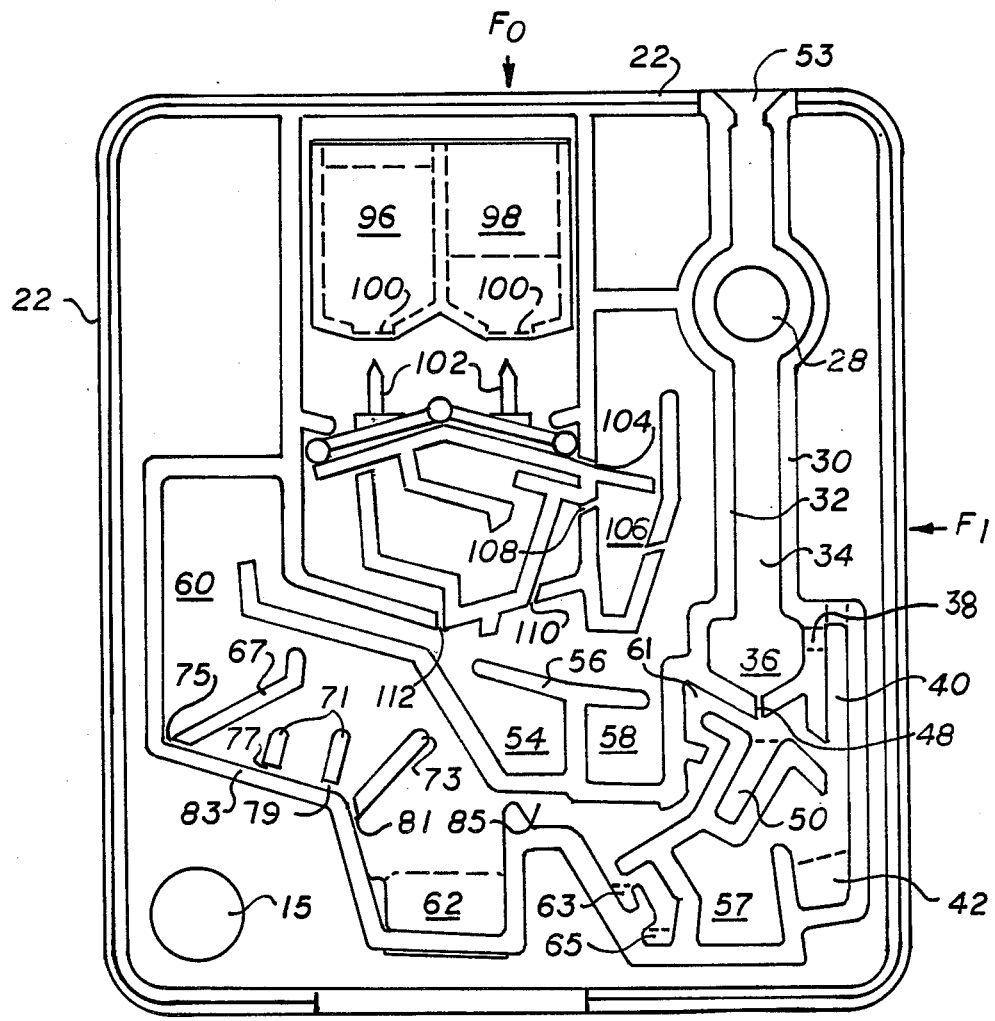
FIG. 5 is a plane view of another embodiment for a sample processor card of the invention having channels and chambers for handling the reagent portion of said invention.
Figure 9:
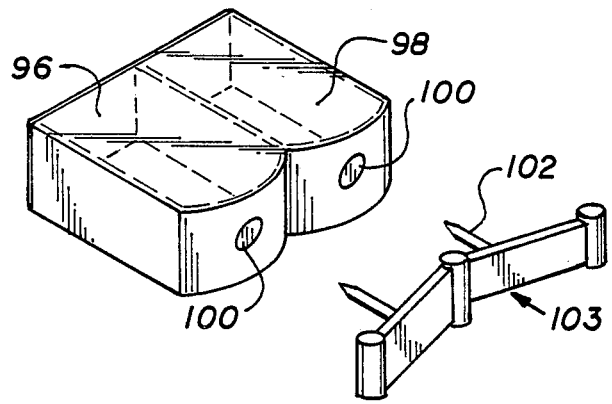
FIG. 9 is a view of another embodiment for a reagent container of the invention.

Another means for releasing the reagent and/or diluent is shown in FIGS. 5 and 9. The chambers 96 and 98 are substantially a closed container with a portion 100 being adapted to being punctured by an impinging means 102 positioned by an impinging means apparatus 103. Typically the impinging means 102 are spike or needle shaped and are located by the apparatus 103 such that the reagent chamber 96 is forced onto the impinging means 102 through the application of centrifugal force. The reagent container can include a plurality of chambers adapted to be punctured by some puncturing means.

Figure 4:
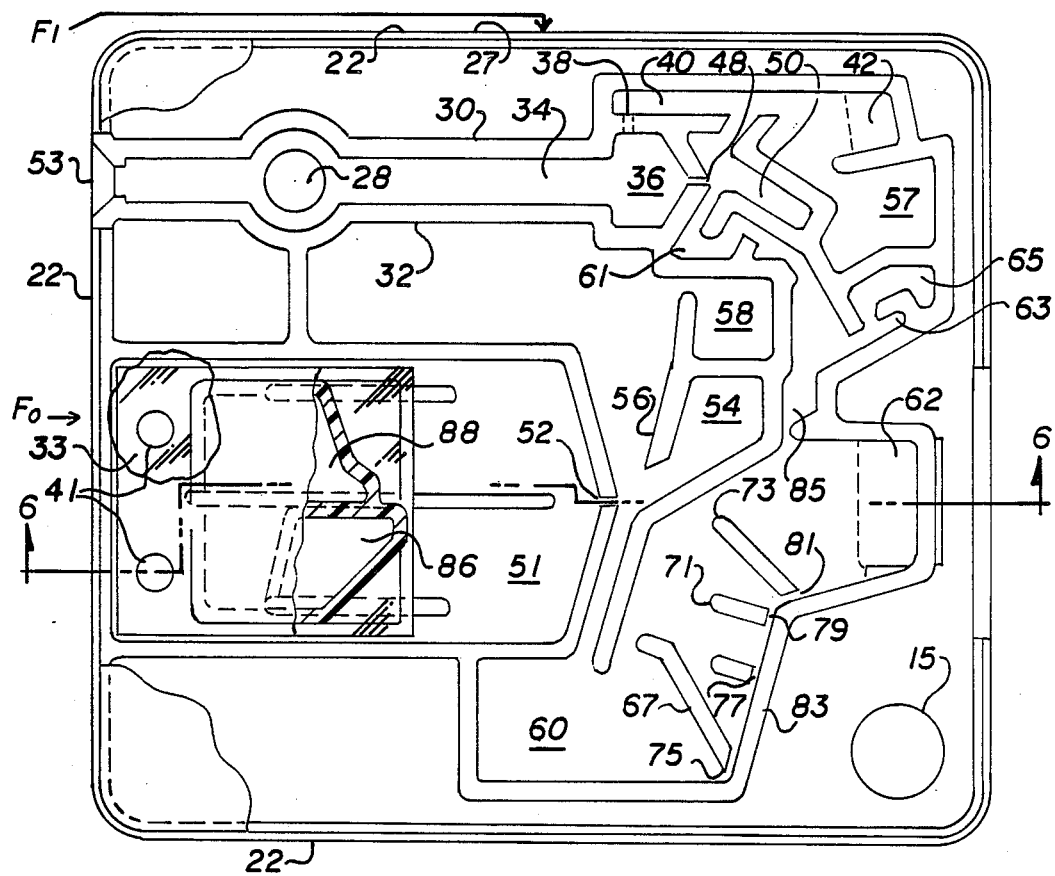
FIG. 4 is a plane view of one embodiment for a sample processor card of the invention.

In many chemical tests, it is preferred to package the reagent and a diluent therefor in separate chambers 86 and 88 as shown in FIG. 4 or 96 and 98 as shown in FIG. 5. In the embodiment of FIG. 4, the strip 33 serves to seal the lower portions of both the reagent chamber 86 and the diluent chamber 88 to maintain the reagent and diluent separate. In the case of the reagent chambers as shown in FIG. 5, they are by their construction separated. Nevertheless, the reagent and diluent chambers, being integral with each other, are displaced together in response to the application of centrifugal force to the card 27 and both reagent and diluent can be released. In FIG. 4 the reagent chamber 86 is positioned slightly forward, in the direction $F_0$ of the centrifugal force, of the diluent chamber 88, so the regent is released prior to release of diluent. In FIG. 5 one chamber can be released prior to the other by either adjusting the length of the impinging means 102 or by positioning one reagent chamber slightly forward of the other reagent chamber.

In the use of the sample processor card of this invention, a blood sample is added to the card as described above, and then the card is positioned in the holder 16 in the centrifuge, insuring that the pin 21 for alignment of the sample processor card with the holder 16 passes through the corresponding key opening 15 extending through the sample card 27.

The card and the holder are positioned initially so that the blood well and reagent container are closest to the center of rotation of the plate member 10 to insure that the centrifugal force exerted on the sample processor card 27 during the initial rotation of the first plate member 10 is exerted in the direction $F_0$ as shown in FIG. 4 or 5 of the drawing. Thus, after the sample of blood is placed in the blood well and the plate member 10 rotated at high speed to develop centrifugal force, that centrifugal force serves to (a) release the diluent and reagent from their respective chamber and (b) move the blood sample inserted into the blood well 28 down the capillary slot 34 under the effect of the centrifugal force.

Downstream of the capillary slot 34 is a blood holding chamber 36 which is filled with the blood sample deposited into the card. Thus, the blood holding chamber 36 operates as a gross measure, selecting a predetermined quantity of blood sufficient to fill the chamber 50 as described hereinafter. Any blood in excess of the quantity filling chamber 36 passes through an opening 38 defined by a wall of the measuring chamber 36. Thus, the excess blood passes through an excess blood slot 40 to overflow chamber 42 located downstream of the excess blood slot 40. The presence of blood in the overflow chamber 42 can thus be used to confirm to the user that the blood sample deposited in the blood well was of a volume sufficient to completely fill the separating chamber 50.

In the preferred practice of the invention, it is frequently desirable to provide the apparatus with optical means positioned to detect the presence of blood in the overflow chamber 42 to thereby confirm that the sample provided was of a sufficient volume. For that purpose, the apparatus (FIG. 2) may include a source of light 44 and a detector 46, one or the other being positioned above the rotating plate 10 and the latter being positioned beneath the holder 16 in the alignment with the overflow chamber 42 and opening 25 as shown in FIG. 3 to detect the presence of blood in the overflow chamber 42.

In the preferred embodiment of the invention, the excess blood opening 38 is larger than the exit capillary 48 of the holding chamber 36 to insure that excess blood is rapidly discharged through the excess blood opening 38 and into the overflow chamber 42. Any quantity of blood in excess to the capacity of the overflow chamber 42 can thus spill over into an auxiliary blood overflow chamber 57.

As centrifugal force continues to act on the blood in the holding chamber 36, it is discharged into a blood separating chamber 50 in which blood is subjected to centrifugal force to separate the solid particulate matter from the fluid phase, any excess spilling over blood separating chamber 50 to the blood overflow chamber 42. As will be appreciated by those skilled in the art, the blood thus introduced to the separating chamber 50 is in effect spun down by the centrifugal force acting in the direction $F_0$ in FIG. 4 or 5 to separate the solid matter from the liquid, the solid matter being more dense than the liquid to thereby form a layer of solid matter at the lower portion of the blood separating chamber 50.

As will be appreciated by those skilled in the art, the release of the diluent and reagent from their respective chambers can occur simultaneously with the movement by centrifugal force of the blood sample down the capillary slot 34. Alternatively, it is possible, and sometimes desirable, to provide a multi-speed operation, a lower speed below a threshold level at which the diluent and reagent are released but one at which the blood is still displaced downwardly through the capillary slot. That technique permits the blood to be separated in the blood separating chamber 50 before the diluent and reagent are released from their respective chambers. Thus, after the blood has been separated in the blood separating chamber 50, the speed of the centrifuge can be increased to effect release of the diluent and reagent.

In either case, the particular configuration of the diluent and reagent chambers, as described above, permit the reagent to be released before the diluent. In the case of FIG. 4 the reagent passes into the chamber 51, through the restricted opening 52 and into the reagent measuring chamber 54. The diluent, released after the initial release of the reagent, likewise passes into the chamber 51 and into the reagent measuring chamber 54, with any excess spilling over the baffle 56 into the reagent overflow chamber 58.

As will again be appreciated by those skilled in the art, alternatives with respect to the use of the reagent can be employed. For example, a solid reagent can be employed and positioned as a pellet in reagent measuring chamber 54 which is activated on release of the diluent as the diluent flows into the reagent measuring chamber 54. Other physical forms of reagent may likewise be used, such as a reagent gel, which would likewise be positioned in the reagent measuring chamber 54.

Alternatively, the solid reagent could be present as a coating on the walls of the reagent measuring chamber 54 which is dissolved when the diluent is released and passed into the reagent measuring chamber 54 as described above. Such a coating of reagent can also be applied to other areas of the card, notably the mixing chamber 60 and/or the cuvette chamber 62, both of which are described more fully hereinafter.

One important concept of the present invention is that the reagent measuring chamber 54 measures a precise, predetermined amount of reagent and diluent. This procedure can also be accomplished by separate reagent measure chambers for the reagent and diluent which have overflow chambers to remove the excess. The liquids can then be mixed by separate communicating channels as depicted in FIG. 5.

As shown in FIG. 5 the reagent and diluent or another reagent can be released and pass through channels and chambers to premeasure, mix or delay their introduction to the sample being tested. For example, in one aspect, reagent can be released from chamber 98 and flow through vent 104 where it enters a measuring chamber 106 then passing through vents 108 and 110 to then travel to the mixing chamber 60. Meanwhile, reagent from chamber 96 can pass directly to measuring chamber 54 via vent 112. In another aspect vents can be provided at other points to change the flow of either reagent subject to the centrifugal forces. Thus, reagent can be added first to the sample then another reagent passing through a tortuous path can be subsequently added to the first reagent/sample mixture.

Once the reagent (mixed with diluent) has been measured in the reagent measuring chamber 54 and the blood separated in the blood separating chamber 50, the card is rotated 90° so that the centrifugal force is now acting in the second direction $F_1$ as shown in FIGS. 4 and 5. After rotation of the card, the centrifugal force thus displaces the measured quantity of reagent and/or diluent from the reagent measuring chamber 54 to a mixing chamber 60. At the same time, the liquid constituent of the blood sample or a portion thereof is transferred to a sample holding chamber 61 downstream of the separating chamber 50. (Downstream as used in that sense is downstream in the direction of the centrifugal force when it is acting in the direction $F_1$ as shown in FIGS. 4 and 5.)

The sample card is then again rotated back to the original position where the centrifugal force is acting in the first direction $F_0$ as shown in FIGS. 4 and 5. In that position, the centrifugal force causes the sample in the sample holding chamber 61 to be conveyed to the sample measuring chamber 63, with any excess sample overflowing sample measuring chamber 63 to a sample overflow chamber 65.

Simultaneously, on rotation of the card to the position where the centrifugal force is acting in the direction $F_0$ as shown in FIGS. 4 and 5, the reagent and/or diluent in the mixing chamber 60 is displaced in a downstream direction. Positioned in the mixing chamber 60 are a series of baffles 67, 71, and 73, which, along with the lateral wall 83 of the mixing chamber 60, define a series of restricted openings 75, 77, 79, and 81. The purpose of these restricted openings is to generate turbulence in the reagent (mixed with diluent) as it flows from the upper portion of the mixing chamber 60 toward the cuvette chamber 62, more fully described hereinafter. As the reagent and/or diluent passes through those series of openings, the resulting turbulence insures that complete mixing of the components will be achieved.

Thus the reagent is moved under the effect of the centrifugal force in the first or $F_0$ direction through the restricted openings 75, 77, 79 and 81 into the cuvette chamber 62. Since the reagent, at this stage of the operation, is unmixed with the sample, the sample remaining in the sample measuring chamber 63, the operator is permitted to take an optical reading of the reagent itself, prior to the time that it is mixed with the sample.

For the purpose of determining the optical characteristics of the reagent mixed with the diluent before contact with the sample, use can be made of a light source 64 and a light detector 64', one being positioned above the card holder 16 and the other beneath it, again with an opening in the card holder 16 to permit the transmission of light from the source 64 to the detector 64' through the cuvette chamber 62. This is sometimes a desirable operation, particularly when the measurements being taken on the sample are to be optical characteristics such as absorbance. The reading taken on the reagent before contact with the diluent enables one to correct the final readings for any absorbance contributed by the raw reagent. That technique can also be used to enable the operator to determine that the reagent was of high quality, and had not been degraded through the passage of time or by contact with an adverse environment.

After the operator has had an opportunity to monitor the characteristics of the reagent in the cuvette chamber 62, the sample processor card is again rotated 90° so that the centrifugal force is again acting in the second direction $F_1$ as shown in FIGS. 4 and 5 of the drawing. The centrifugal force thus causes the sample, in the sample measuring chamber 63, to pass through a chamber 85 and into the mixing chamber 60 where the sample, along with the reagent from the cuvette chamber 62, pass together through the series of restricted openings 81, 79, 77 and 75 into the upper portion of the mixing chamber 60 to effect mixing of the sample with the reagent. Because of the configuration of the baffle separating the sample measuring chamber 63 from the sample overflow chamber 65, any sample in the overflow chamber 65 is retained therein.

After the sample and reagent reach the upper portion of the mixing chamber 60, the card is again rotated 90° so that the centrifugal force is once again acting in the direction $F_0$. That rotation of the card causes the sample and reagent in the upper portion of the mixing chamber 60 to again pass through the restricted openings 75, 77, 79 and 81. In other words, mixing of the sample with the reagent occurs by means of passages through the restricted openings 75 to 81 as described. The mixture of the sample and reagent is thus displaced under the centrifugal force acting in the direction $F_0$ into the cuvette chamber 62. At this stage in the procedure, optical readings of the reaction product of the sample and reagent can be taken incrementally or at the final stage by means of the light source 64 and detector 64' in the manner described above.

Alternatively, continuous mixing can be achieved by again rotating the card so that the reagent and sample mixture is again displaced through the restricted openings while the chemical reaction between the two is ongoing during the incubation period of the reaction.

It is an important concept of the present invention that the centrifugal force operating on the fluids in the sample processor card be at a relatively high level so that the centrifugal force greatly overwhelms the fluid surface tension. That insures that the meniscus of the fluids defines a section of a substantially circular cylinder about the center of the centrifuge plate. When the sample processor card is rotated, the fluids pour from one chamber to another in the same way as if the chamber size and fluid quantities were much larger. If the rotation were such that substantially lower centrifugal forces were created, the fluids would tend to pour in large droplets and give quite variable results. It has accordingly been found that best results are usually achieved when the plate member is rotated at speeds sufficient to create centrifugal forces of at least 500 g's.

It will be understood that various changes and modifications can be made in the details of construction, procedure and use without departing from the spirit of the invention, especially as defined in the following claims.

What we claim is:

1. A sample processor card for carrying out chemical tests under centrifugal force, said centrifugal force being applied in at least two directions relative to said card by the orientation of the card on a centrifuge rotor, said card comprising:
    means defining an outer enclosure having a plurality of walls defining therein:
    (a) inlet means for supplying a sample to the card, sample measuring chamber means communicating with said inlet means to measure a volume of sample, and a sample overflow means communicating with the inlet means and the sample measuring chamber means, said sample measuring chamber means and said sample overflow means being disposed such that centrifugal force acting in a first direction relative to said card moves sample into said sample measuring chamber means, with excess sample moving into said sample overflow means;
    (b) reagent containing means for supplying at least one reagent;
    (c) mixing chamber means communicating with said sample measuring chamber means and said reagent containing means and disposed such that centrifugal force acting on the card in a second direction relative to the card admits said measured volume of sample and said reagent into said mixing chamber means; and
    (d) cuvette means communicating with the mixing chamber means;
    wherein said sample measuring chamber means, said reagent containing means, said mixing chamber means and said cuvette means are arranged in said enclosure such that movement of sample or reagent among said sample measuring chamber means, said reagent containing means, said mixing chamber means and said cuvette means can be accomplished solely by changing the orientation of the processor card relative to a centrifuge rotor without substantially lowering the magnitude of centrifugal force.

2. The card as defined in claim 1 wherein the enclosure further defines sample separating chamber means disposed intermediate and in communication with the inlet means and the sample measuring chamber means and adapted to separate, under centrifugal force in one of said first and second directions, constituents of the sample.

3. The card as defined in claim 1 wherein the card further includes means for dispensing reagent solely in response to centrifugal force applied to the card.

4. The card as defined in claim 3 wherein the means for dispensing reagent includes means for dispensing reagent and means for dispensing diluent for the reagent.

5. The card as defined in claim 3 wherein the means for dispensing reagent includes reagent chamber means adapted to contain the reagent and strippable sealing means closing the reagent chamber means whereby the sealing means is stripped from the reagent chamber means in response to the application of centrifugal force applied to the card to release reagent from the chamber means.

6. The card as defined in claim 5 which includes diluent chamber means positioned adjacent to the reagent chamber means, the sealing means closing the reagent chamber means and the diluent chamber means whereby the application of centrifugal force releases reagent and diluent.

7. The card as defined in claim 6 wherein the reagent chamber means is positioned forward of the diluent chamber means whereby the reagent is released prior to the release of diluent in response to the application of centrifugal force.

8. The card as defined in claim 5 which includes means for securing to the card the sealing means whereby the application of centrifugal force to the card displaces the reagent chamber means in the direction of the centrifugal force to strip the sealing means from the reagent chamber means to thereby release the reagent.

9. The card as defined in claim 3 wherein the means for dispensing reagent comprises a reagent chamber means having a portion thereof adapted to be punctured by an impinging means in response to centrifugal force applied to said card.

10. The card of claim 9 which includes a diluent chamber means having a portion thereof adapted to be punctured by an impinging means in response to centrifugal forces applied to said card.

11. The card as defined in claim 1 wherein said enclosure further defines a plurality of channel and chamber means disposed intermediate and communicating with said reagent containing means whereby the flow and measurement of said reagent and/or diluent can be adjusted.

12. The card as defined in claim 1 wherein the enclosure defines a plurality of baffles defining restricted openings positioned between the mixing chamber means and the cuvette means so that the reagent and sample pass through the restricted openings while flowing, in response to centrifugal force applied to the card in either direction, between the mixing chamber means and the cuvette means to facilitate intimate mixing between the reagent and the sample.

13. The card as defined in claim 1 wherein the enclosure defines a key opening extending into the card and adapted to receive a key to insure that the card is properly registered in a centrifuge.

14. The card as defined in claim 1 wherein the means defining the outer enclosure further includes substantially parallel upper and lower surfaces and side walls having a double bevel with an apex between said upper and lower surfaces, said apex adapted for securing the card to a centrifuge rotor.

15. A method for carrying out chemical tests under centrifugal force on a centrifuge rotor, comprising the steps of:
  (a) supplying a sample to be tested to a sample processor card having
    (1) inlet means for supplying a sample to the card, sample measuring chamber means communicating with said inlet means to measure a volume of sample, and a sample overflow means communicating with the inlet means and the sample measuring chamber means, said sample measuring chamber means and said sample overflow means being disposed such that centrifugal force acting in a first direction relative to said card moves sample into said sample measuring chamber means, with excess sample moving into said sample overflow means;
    (2) reagent containing means for supplying at least one reagent;
    (3) mixing chamber means communicating with said sample measuring chamber means and said reagent containing means and disposed such that centrifugal force acting on the card in a second direction relative to the card admits said measured volume of sample and said reagent into said mixing chamber means; and
    (4) cuvette means communicating with the mixing chamber means;
  (b) subjecting the card to a substantially uniform and continuous centrifugal force acting in a first direction relative to the card to move sample into said sample measuring chamber means, with excess sample moving into said sample overflow means;
  (c) reorienting the card relative to a centrifuge rotor to change the effective direction of centrifugal force acting thereon to a second direction, thereby to contact the sample with reagent and effect a chemical reaction therebetween, said contact being accomplished solely by changing the relative direction of centrifugal force and without substantially lowering the magnitude of centrifugal force; and
  (d) measuring the reaction product of the sample and reagent.

16. A method as defined in claim 15 which includes the step of centrifugally separating the sample constituents before contacting the sample with reagent.

17. A method as defined in claim 15 which includes the step of releasing reagent from a closed container in response to centrifugal force.

18. A method as defined in claim 15 which includes the step of mixing reagent with the sample.

19. A method as defined in claim 18 wherein the sample and reagent are mixed by passing through at least one restricted opening under the effect of centrifugal force.

20. A method as defined in claim 19 wherein the reagent and sample are passed through the restricted opening by centrifugal force acting in a first direction and the card is rotated to change the direction of the centrifugal force to pass the reagent and sample again through the restricted opening in the opposite direction.

21. A method as defined in claim 15 which includes the step of measuring a substantially precise amount of reagent and/or diluent for contacting the sample and retaining excess reagent and/or diluent.

* * * * *